United States Patent [19]
Creekmore

[11] Patent Number: 4,531,911
[45] Date of Patent: Jul. 30, 1985

[54] COMBINATION SINGLE/TWIN EDGEWISE ORTHODONTIC BRACKET

[76] Inventor: Thomas D. Creekmore, 1620 Fountainview, Houston, Tex. 77057

[21] Appl. No.: 557,877

[22] Filed: Dec. 5, 1983

[51] Int. Cl.³ .............................................. A61C 7/00
[52] U.S. Cl. .......................................... 433/8; 433/9
[58] Field of Search ...................... 433/8, 10, 9, 15, 16

[56] References Cited

U.S. PATENT DOCUMENTS

| 2,854,747 | 10/1958 | Lewis | 433/8 |
|---|---|---|---|
| 3,164,901 | 1/1965 | Wallshein | 433/16 |
| 3,504,438 | 4/1970 | Wittman et al. | 433/8 |
| 3,765,091 | 10/1973 | Northcutt | 433/9 |

*Primary Examiner*—Robert Peshock
*Attorney, Agent, or Firm*—Gunn, Lee & Jackson

[57] ABSTRACT

A combination single/twin edgewise orthodontic bracket incorporating twin tie wings to promote twin ligating capability and over-rotation capability, and also incorporating an intermediate section of single bracket width that defines a precision archwire slot for receiving an edgewise archwire of rectangular cross sectional configuration to promote orthodontic treatment with the edgewise orthodontic technique. Relief grooves between the upper and lower tie wings extend outwardly from the ends of the precision archwire slot and are relieved in both width and depth as they traverse each tie wing mesially and distally to provide for efficient over-rotation control. The relief grooves cooperate with the central bracket section to permit the fullest expression of the advantages of interbracket width. The single/twin tying, bracket features may be employed in a wide variety of bracket structures including "T" brackets, which accommodate loops more conveniently while preserving the advantages promoted by spaced ligating tie wings. Transverse ligature slots formed in the proximal edges or ends of the bracket permit application of efficient force vectors to the edgewise archwire even when the archwire slot is severely angulated to maintain optimum seating of the archwire within its slot.

29 Claims, 21 Drawing Figures

COMBINATION SINGLE/TWIN EDGEWISE ORTHODONTIC BRACKET

FIELD OF THE INVENTION

This invention relates generally to orthodontic brackets which are utilized by orthodontists to accomplish accurate movement and positioning of the teeth of a patient. More specifically, the present invention concerns the provision of a specific orthodonitic bracket system and therapeutic technique which combines certain advantages promoted by single ligating tie wing type edgewise orthdontic brackets with the advantages achieved by edgewise orthodontic brackets having twin ligating tie wings.

BACKGROUND OF THE INVENTION

Although a number of differing orthodontic techniques exist, the majority of orthodontists in practice in the United States, at this time, utilize one of two basic orthodontic therapy techniques in their treatment of patients. These basic techiques are the "light-wire" technique and the "edgewise" technique. Light-wire appliances were first designed and presented to the profession by an Australian orthodontist, R. P. Begg, who introduced the idea of differential force control. Since some types of tooth movements evoke more tissue resistance than others, and some movements occur faster than others, Begg reasoned that by selectively choosing the movements required and relating the reciprocal reactions properly, tooth movement might be accomplished in orderly manner. The Begg light-wire technique is characterized by a number of significant features. Brackets are fixed to all of the teeth of the patient anterior to and including the first molars. Archwires are round in cross-section and provide archform and leveling of the teeth. Archwires are loosely pinned to the bracket and are not ligated. The Begg brackets provide a single point contact with the archwire to minimize friction and permit the teeth to slide, rotate, tip and torque freely. For purposes of this invention, tipping movement of the teeth is defined as rotation of the long axis of a tooth in the mesia-distal direction. Torque movement means rotation of the long axis of a tooth in a buccal-lingual direction. Rotation is defined as movement of a tooth about its long axis in a mesial-distal direction. Tip, torque and rotation are accomplished by auxiliaries and not by the fit between the archwire and bracket as in the edgewise technique. Extra oral anchorage is not used. Reciprocal anchorage is provided for by selectively utilizing teeth posterior to extracton sites to retract teeth anterior to the extraction sites with intra and inter maxillary elastics. The light-wire appliances are now several and varied from the original design, although all employ sophisticated concepts in theories of tooth movement and anchorage control. Standard light-wire therapy does not utilize extra-oral traction, frequently involves extraction of teeth and typically employs more auxiliaries than conventional edgewise therapy.

The most widely utilized orthodontic therapy technique in this country, and the technique to which this invention is directed, is the "edgewise" technique, which was brought to the industry by Dr. Edward H. Angle. It should be understood, however, that this invention is also applicable to other orthodontic techniques such as the multi-phase and twin wire edgewise techniques, for example. In the beginning stages of edgewise therapy, archwires of circular cross-sectional configuration are employed. The greater flexibility of the round wire permits greater raange of movement of malposed teeth with less force to the teeth. For secondary and finishing therapy, the edgewise technique typically incorporates a multibanded precision appliance consisting of a labial archwire of rectangular cross-section that is ordinarily of greater dimension at the sides than at the edges thereof. The archwire is fitted and ligated with metal ligature wire, or ligature elastics, or any other suitable form of mechanical retention, into precision mating horizontal archwire slots that are formed in brackets on all of the permanent teeth including first molars and frequently second molars. The archwire terminates in buccal tubes each having a rectangular passage through which the ends of the rectangular archwire extend. The archwire, which may be composed of stainless steel or precious alloy, is typically positioned with its narrow dimension or edge lying against the labial and buccal surfaces of the teeth. This feature gives the technique its name "edgewise." The edgewise technique makes control possible in all directions and any individual tooth may be moved simultaneously in three directions; for example, an incisor may be moved lingually, distally and rotated around its long axis with one adjustment of the archwire. The rectangular cross-sectional configuration of the archwire permits it to be twisted to a desired extent and, being of spring-like nature, the twisting forces will be applied through the archwire to the teeth, thereby inducing a torquing movement of the teeth as the archwire untwists due to spring action and returns to its normal untwisted configuration. The brackets are precision milled to a rectangular shape so that the orthodontist can select precision milled archwires to fit as precisely as desired. Tip, torque and rotation are accomplished by the fit between the archwire and bracket. Extra oral anchorage may or may not be used as desired. Reciprocal anchorage can be provided by extraction of teeth and selectively utilizing teeth posterior to extraction sites to retract teeth anterior to the extraction sites with intra and inter maxillary elastics and/or closing loop archwires. This invention is specifically directed to the edgewise technique and more specifically concerns an orthodontic appliance system that integrates specific advantages that are afforded by edgewise appliances of single and twin ligating capability.

Single tie wing brackets for the edgewise technique typically incorporate a base structure which has a precision active archwire groove that receives a rectangular archwire. A pair of ligating tie wings extend from the bracket base on opposite sides of the precision archwire slot. These tie wings are typically centered with respect to the bracket structure and are therefore intended to be positioned in substantially centered mesio-distal relationship with the facial surface of the tooth to which the bracket is secured. A ligature wire or elastic is looped over each of the tie wings and is passed over the archwire at each end of the slot, thus securing the archwire firmly in its precision slot.

Single brackets provide maximum efficiency in the application of tipping and torquing of teeth but are minimally efficient in rotational control. Initially, rotational control was accomplished by soldering or welding eyelets at the extreme mesial or distal of the band attached to the tooth. The orthodontist could ligate the eyelet to the archwire, pulling that surface closer to the archwire and causing the tooth to rotate about the centrally located bracket. This is a cumbersome and inefficient method of rotational control.

Subsequently, fixed or flexible rotation levers, projecting mesially and distally, were added to the centrally located single bracket. Thus, a rotated tooth would have the rotation wing projecting more facially than the bracket. The archwire would touch the rotation wing and, as the wire is ligated into the bracket, cause the tooth to rotate about the bracket. The rotation lever is adjustable to project more or less to the facial as desired. This permits the orthodontist to select the amount of rotation desired by adjusting the rotation lever rather than adjusting the archwire.

The disadvantage of the rotation lever approach to tooth movement is evident in the initial stages of treatment. The archwire will not touch the rotation lever if a tooth is tipped and rotated severely and will prevent either action from occurring unless the archwire is adjusted to strike the rotation lever when ligated. Thus, initial archwire insertion can be inefficient and require more expertise to ligate.

Twin brackets were introduced to alleviate the inefficient rotation effectiveness of the single bracket. Instead of one centrally located bracket, two brackets were placed at the mesial and distal of the tooth. Thus, when each bracket is ligated to the archwire, the facial surface of the tooth will align itself with the archwire, rotating the tooth.

One of the principles of rotation in orthodontics is over-correction of the original problem to compensate for the rebound or relapse tendency. This is especially indicated for rotated teeth. Twin brackets do not have the capacity for over-rotation. For over-rotation with twin brackets, the archwire must be bent or some auxiliary must be added to push the mesial or distal portion of the bracket away from the archwire. Further, single edgewise brackets, without rotation levers, are also lacking in over-rotation control capability which will be discussed in more detail hereinbelow.

One of the more important advantages of single brackets is the advantage that is afforded by the active length of archwire existing between the points of connection to adjacent brackets. This is known as "interbracket width." Since the connecting point between adjacent single brackets is established at substantially the center of the adjacent teeth, the archwire length, and thus the interbracket width, extends to points near the centers of adjacent teeth. The lengthy archwire span that exists between single brackets allows lower magnitude forces to be applied to the teeth over longer periods of time as compared to circumstances where the interbracket width is limited and the archwire span is short as is the case when conventional twin brackets are employed. The long span of archwire may be twisted much further without exceeding the elastic limit of the archwire material and causing permanent yielding or deformation of the archwire. Where the archwire between brackets is of limited length, which is typical where twin brackets are employed with the edgewise technique, application of large magnitude forces to the teeth can occur with only minimal twisting or flexing of the archwire. Thus, after limited movement of the teeth occurs, the forces induced by the short archwire interbracket width dissipate quickly, thereby requiring frequent adjustment in order to maintain optimum force application for efficeint tooth movement. Of course, it is evident that frequent adjustment of orthodontic appliances necessitates frequent visits by the patient for adjustment of the orthodontic appliance and is disadvantageous to the patient. Such frequent adjustment also requires a significant amount of chair time in the office of the orthodontist, thereby either increasing the cost of treatment to the patient, or minimizing the commercial advantage of orthodonitc treatment on the part of the doctor. It is desirable, therefore, to provide a system for orthodontic treatment wherein patient visits are minimized and chair time is also minimized, to the mutual benefit of both the patient and doctor.

Twin brackets for the edgewise technique have been employed for a considerable period of time. Twin brackets typically incorporate a pair of spaced projections that extend from or are formed by the bracket base, each projection being formed to define a precision active archwire slot segment. The spaced active archwire slot segments cooperate to define a precision archwire slot having the effect of extending the entire length of the base. Each of the projections is provided with upper and lower tie wings, thereby defining a bracket structure with four tie wings, the tie wings and the effective archwire slot terminating at the opposed side portions of the base structure. With the base structure centered in respect to the tooth to be moved, the tie wings will be positioned in pairs at opposed sides of the tooth, thereby defining bracket structure with efficient rotation control. The orthodontist may utilize ligature wire or elastic members between selected tie wings and the archwire to develop the force moments that are necessary for efficient rotational control.

One of the typical disadvantages in utilizing twin brackets is the minimization of interbracket width that exists as the result of positioning the tie wings at opposed side portions of the bracket structure. Ordinarily, as explained above, minimization of interbracket width, in conjunction with the edgewise orthodontic technique, suffers the disadvantage of requiring frequent patient visits and increasing chair time because of the necessity for frequent adjustment of the appliance in order to maintain the force levels within the optimum range for efficient tooth movement.

Another significant disadvantage of twin brackets is that the spaces that are typically available between the tie wings of adjacent brackets leave insufficient room between the teeth for closing loops and tie-back loops. It is desirable, therefore, to provide an orthodonitic bracket structure that affords the advantages offered by twin brackets and yet provides ample space between certain tie wings of adjacent brackets to facilitate efficient use of closing loops and tie-back loops in conjunction with edgewise orthodonitic therapy.

SUMMARY OF THE INVENTION

It is a principal feature of the present invention to provide a novel single/twin orthodontic bracket system which allows the application of over-rotation control forces to the teeth.

It is also a feature of the present invention to provide a novel orthodontic bracket system employing twin tie wings for effective rotational control and also providing the length of interbracket width ordinarily afforded by single brackets for maintenance of maximum active archwire length between adjacent brackets.

It is an even further feature of this invention to provide a novel orthodontic bracket system which employs twin tie wings for optimum rotational control and yet also employs a centrally oriented bracket section forming a precision machined active archwire slot which promotes controlled tipping and torquing movement of teeth, such as is typically accomplished through the use of single tie wing type brackets in accordance with conventional edgewise therapy.

Among the several objects of this invention is contemplated the provision of a novel orthodontic bracket system utilizing twin tie wing capability and yet providing sufficient space between certain adjacent brackets for efficient employment of tie-back loops and closing loops.

It is also a feature of this invention to provide a novel single/twin orthodontic bracket system having greater rotational control and over-rotation capability as compared to conventional twin brackets.

It is an even further feature of this invention to provide a novel orthodontic bracket concept enabling an orthodontist to selectively utilize various combinations of rotation and over-rotation control, torque and tipping simply through selection of various twin brackets that each embody a centralized single bracket section forming at least one precision active archwire slot in accordance with the principles of this invention.

Another feature of this invention is to provide a novel orthodontic bracket structure which permits application of efficient force vectors from the ligature member to the edgewise archwire.

It is another feature of this invention to provide a novel single/twin orthodontic bracket which is of simple nature, is comparable with other orthodontic brackets from the standpoint of ease of installation and use and suffers no competitive disadvantage in comparison with other similar orthodontic bracket systems.

Briefly, combination single/twin orthodontic brackets, according to this invention, incorporate a base or body structure which is adapted to be secured in immovable relation with a tooth. The base may be attached to bands that are positioned about the teeth and cemented in place or the base may be adapted for direct bonding to the tooth structure. In one form of the invention, the base defines a pair of outwardly extending paced projections each of which define upper and lower tie wings for ligating, thereby presenting an orthodontic bracket structure in the general form of a twin bracket system. Between the spaced tie wing projections is formed an intermediate archwire active section which may be separate from the tie wing projections, if desired, or, in the alternative, may be an integral part of a single projection defining spaced tie wing portions and an intermediate archwire active section. The intermediate section of the orthodontic bracket is machined to define a precision active archwire slot constructed in accordance with the edgewise therapy technique. The spaced tie wing projection portions of the orthdontic bracket structure are each formed to define archwire relief grooves through which the archwire extends. These grooves are not cooperatively active with the archwire, but rather define archwire relief which allows archwire controlled tooth movement to be accomplished by archwire transmitted force activity solely from the intermediate section of the bracket. The inactive archwire grooves in the tie wing projection portions of the bracket structure may be formed to define surfaces that diverge in both width and depth from the centermost portions thereof outwardly toward the respective ends of the bracket. Since the surfaces of the archwire grooves diverge outwardly in both occlusal-gingival width and buccal-lingual depth, the archwire grooves provide sufficient structural relief that the tie wing portions of the bracket structure do not interfere with the archwire and thereby permit the precision active slot of the intermediate section of the bracket structure to provide sole archwire responsive tipping and torquing of the teeth. Further, by providing the bracket with an intermediate section and by preventing archwire interference at the twin tie wing portions of the bracket structure, there is defined maximum inter-bracket width between adjacent orthodontic brackets. This feature allows maximum archwire controlling activity, as if the bracket structure were only as wide as the small intermediate section of the bracket.

In another form of this invention, an orthodontic bracket structure may incorporate active archwire slots in both of the twin ligating tie wing portions of the bracket structure. In this case, the archwire slot is formed to define archwire relief only in depth from the intermediate section. Accordingly, the interbracket width defined by the relief between the fulcrum sections of the orthodontic brackets of adjacent teeth is provided primarily for the accomplishment of rotation and over-rotation.

Under circumstances where twin ligating capability is desired and closing loops and tie-back loops are also desired, the combination single/twin orthodontic bracket structure may take a generally "T" shaped form having a pair of spaced ligating tie wings on the upper or lower portions thereof and a centrally oriented ligating tie wing on the opposite portion thereof. The bracket structure will be such as to define a precision active archwire slot intermediate the extremities thereof and with outer portions of the bracket structure relieved so as to receive the edgewise archwire in a noninterfering relation.

Other and further objects, advantages and features of the present invention will become apparent to one skilled in the art upon consideration of this entire disclosure. The form of the invention, which will now be described in detail, illustrates the general principles of the invention, but it is to be understood that this detailed description is not to be taken as limiting the scope of the present invention. It is possible that the invention may take many suitable forms other than that specifically discussed, without departing from the spirit and scope of this invention.

BRIEF DESCRIPTION OF THE DRAWINGS

In order that the manner in which the above recited advantages and features of this invention are attained and can be understood in detail, more particular description of the invention, briefly summarized above, may be had by reference to the specific embodiments thereof that are illustrated in the appended drawings, which drawings form a part of this specification. It is to be understood, however, that appended drawings illustrate only typical embodiments of the invention and are, therefore, not to be considered limiting of its scope, for the invention may admit to other equally effective embodiments.

IN THE DRAWINGS

DETAILED DESCRIPTION OF PREFERRED EMBODIMENT

Referring now to the drawings and first to FIGS. 1-4, an orthodontic bracket incorporating the various features of the present invention is illustrated generally at 10 and includes a base or bracket body portion 12 which is adapted to be secured in immovable relation with a single tooth of a patient undergoing orthodontic therapy. The base 12 may be secured to a metal band encircling the tooth such as by spot welding if desired or, in the alternative, the base structure may be prepared for direct bonding to the enamel surface of the tooth. The base portion of the orthodontic bracket is preferably formed of metal such as stainless steel or a precious metal, but, in the alternative, the base and the other components of the orthodontic bracket structure may be composed of any suitable material capable of being utilized and accomplishment of edgewise orthodontic therapy. The base structure is adapted to be secured to bands or to the teeth of the patient in such manner that the archwire extends near the labial and buccal surfaces of the patient's teeth.

A pair of bracket base projections 14 and 16 extend outwardly from one side of the base structure 12 and may be secured to the base structure such as by welding or, in the alternative, may be formed integrally with the base structure. The bracket base projections are positioned at or adjacent the opposed mesial and distal side edges 18 and 20 of the base 12 thereby allowing forces induced through the bracket base projections to be received at edge portions of the tooth involved and thereby providing the capability of efficiently introducing rotational forces to the tooth. Each of the bracket base projections 14 and 16 incorporate upper and lower ligating tie wings such as shown at 22, 24, 26 and 28. Spaced tie wings such as 22 and 26 define a specified tie wing length of the bracket. Since the base projections 14 and 16 are located at respective side portions of the base structure 12, the upper and lower pairs of ligating tie wings are also positioned in off-center relation to the tooth undergoing therapy. With a ligature wire or elastic band is looped around upper and lower ones of the tie wings and passed across the archwire, a force having a rotational moment is induced through the respective tie wing projection to the base structure 12 and thence to the tooth, thereby inducing rotational movement to the tooth within the alveolar arch. The rotational capability of the orthodontic bracket structure 10 will be discussed in greater detail hereinbelow especially in relation to inducement of over-rotational forces to the teeth of the patient.

The orthodontic bracket incorporates an intermediate archwire active section 30 which is secured to or formed integrally with the base structure 12 and which is positioned intermediate the twin base projections 14 and 16. The intermediate section 30 is machined or otherwise formed to define a precision active archwire slot 32 having generally planar spaced side walls 34 and 36 that are precisely parallel and are adapted to receive an edgewise archwire of rectangular cross-sectional configuration in precision fitting relation therebetween. Although the archwire slots of the various brackets are shown herein as being substantially perpendicular to the base as viewed in cross-section, it is to be understood that variously angulated archwire slots may also be employed within the spirit and scope of this invention for the application of various torque values for different teeth. During initial tooth movement, the archwire is typically of circular cross-section to promote flexibility to thereby accommodate gross malocclusion. During the later stages of edgewise therapy, the archwire will be of rectangular cross-section and tooth moving forces will be transmitted from the archwire to the bracket by virtue of the precision interfitting relation of the rectangular archwire within the rectangular archwire slot. The archwire slot 32 is also defined by a flat bottom of wall 38 which is in spaced parallel relation with the upper surface 40 of the intermediate section, the spacing being such that the upper surface of the rectangular archwire is positioned in substantially coextensive relation with the upper surface. It should be borne in mind, however, that the upper portion of the archwire may be positioned above or below the upper surface 40 of the fulcrum section without departing from the spirit and scope of the present invention.

As described above, it is desirable to provide an orthodontic bracket structure with twin ligating capability without suffering the restriction to rotational control that is typical with conventional twin orthodontic brackets. In accordance with the present invention, movement of the teeth through the use of typical edgewise therapy is accomplished through the intermediate archwire active section of the orthodontic bracket 10. Since the intermediate section 32 is substantially centered in relation to the base structure 12 and the precision archwire slot 32 is of the minimal length typically found in single orthodontic brackets, the effective interbracket spacing between adjacent brackets will extend from the respective end portions of the archwire slot in the intermediate archwire active section only. The spaced twin projections 14 and 16 will have no active archwire reaction capability and, therefore, would have no effect on the torque and tipping control of the teeth. Each of the projections 14 and 16 is formed to define archwire relief which may take the form of an archwire groove, such as shown respectively at 42 and 44. The respective archwire grooves of the twin projections are formed such that the surfaces thereof diverge or flare both occlusally and gingivally as the grooves traverse the base projection (mesially and distally). As shown particularly in FIGS. 1 and 2, the twin projection 14 is formed to define diverging groove surfaces 46 and 48 that are shown to be of substantially planar configuration. It should be borne in mind that the particular configuration of surfaces 46 and 48 and the form of the archwire groove is not controlling in regard to the concept of this invention, it only being necessary that the grooves 42 and 44 be of sufficiently relieved configuration to permit the archwire to be allowed to be bent and/or twisted from the archwire slot 32 outwardly preferably without contacting the wall surfaces of the respective archwire groove. It should be borne in mind that in the early stages of orthodontic therapy, especially in cases of gross malocclusion, the archwire may require sufficient bending and/or twisting that it comes into contact with an outer edge defined by the archwire relief groove. Logically, interbracket width is then limited. As soon as the maloccluded teeth begin to move in response to therapy, the outer edge of the bracket will move out of contact with the archwire. As soon as this occurs, maximum interbracket width will be established. The diverging surfaces 46 and 48 provide sufficient archwire relief to allow for considerable bending and twisting of the archwire between the intermediate sections of adjacent orthodontic brackets and thereby permit application of torque through the bracket structure to the teeth in accordance with the conventional edgewise therapy. The archwire groove 42 is also defined by a tapered surface 50 which is in the nature of an inwardly diverging surface tapering inwardly from the bottom surface 38 of the archwire groove 32. The inwardly tapering surface 50 insures that the base projection 14 will not interfere with the rotational capability of the orthodontic bracket and, in fact, the inwardly tapering surfaces of each of the base projections cooperate to provide the bracket structure with an over-rotation control capability. The opposite tie wing projection 16 also defines a diverging archwire groove 52 forming diverging upper and lower surfaces 54 and 56 and an inwardly tapering surface 58. The wide angle of the diverging archwire grooves of each of the base projections allows extensive deformation of the archwire either in bending or twisting over the rather long interbracket length or width that exists between adjacent intermediate sections of brackets on adjacent teeth. Ligature wires, external springs, elastic members and the like may, therefore, be employed to provide controlled rotational forces thus inducing efficient rotational movement of the teeth during orthodontic therapy, such as is typically allowable only through the use of single edgewise brackets. Moreover, these widely diverging grooves of the bracket effectively provide the bracket structure with an over-rotational capability, allowing the teeth of the patient to be moved rapidly until they reach the final positions thereof within the alveolar arch.

The orthodontic bracket 10 provides the orthodontist with the capability of accomplishing tooth movement through utilization of a combination of the features found effective in both single brackets and twin brackets. Single brackets function efficiently because of their long effective interbracket width and because they have the capability of introducing efficient tipping and torquing moments to the teeth. Although the bracket structure of the present invention is of twin bracket length it incorporates an intermediate archwire active section of single bracket width, together with archwire relief grooves in the spaced twin tie wing projections thereof, the bracket structure will achieve both single and twin bracket capability. The bracket will provide the tipping and torquing moments of single brackets and permit the rotation and over rotation control ordinarily afforded only by twin brackets. The feature ordinarily absent or rather ineffective in single orthodontic brackets, i.e., rotational control, is effectively provided for in the bracket design of FIGS. 1–4.

Figure 1:
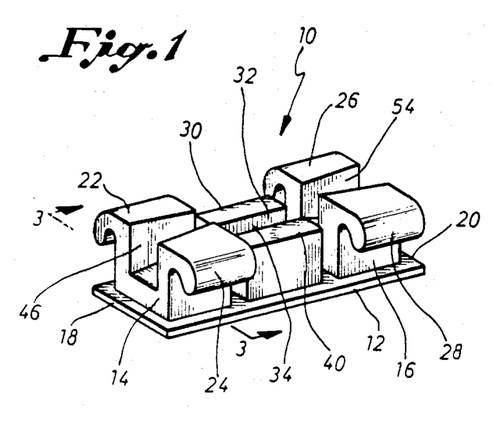
FIG. 1 is an isometric illustration of an orthodontic bracket that is constructed in accordance with the present invention and which incorporates a centrally located archwire active section that is positioned between and is separate from a pair of twin ligating tie wing projections.
Figure 2:
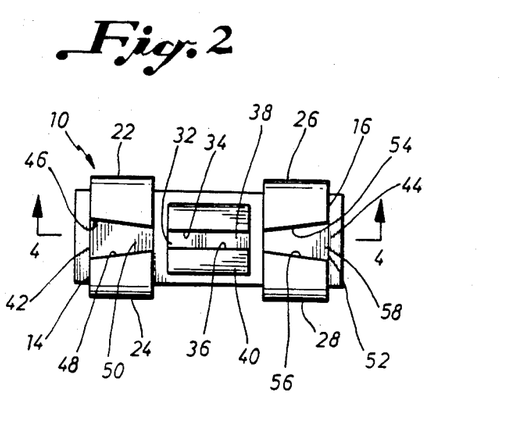
FIG. 2 is a plan view of the orthodontic bracket structure of FIG. 1.
Figure 3:
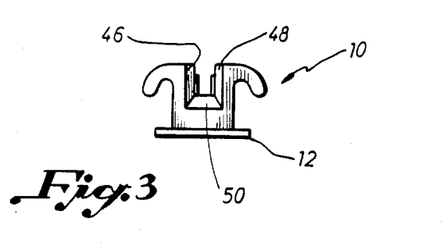
FIG. 3 is an end view of the orthodontic bracket of FIGS. 1 and 2, taken along line 3—3 of FIG. 1.
Figure 4:
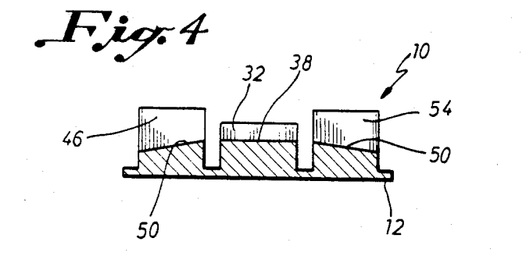
FIG. 4 is a sectional view of the orthodontic bracket structure of FIGS. 1 and 2, the section being taken along line 4—4 of FIG. 2.
Figure 5:
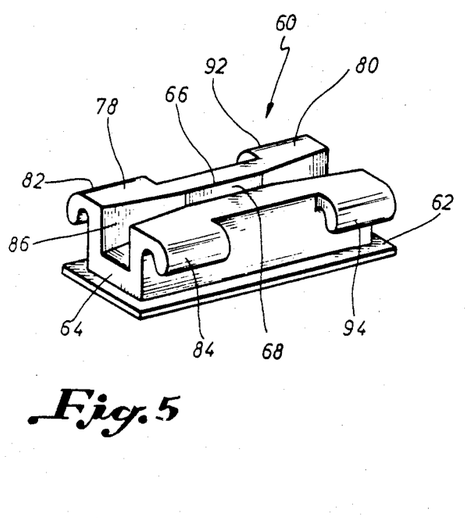
FIG. 5 is an isometric view of an orthodontic bracket that is constructed in accordance with the present invention and represents a modified embodiment.
Figure 6:
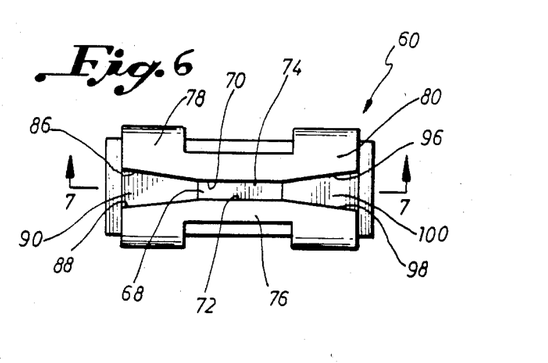
FIG. 6 is a plan view of the orthodontic bracket structure of FIG. 5.
Figure 7:
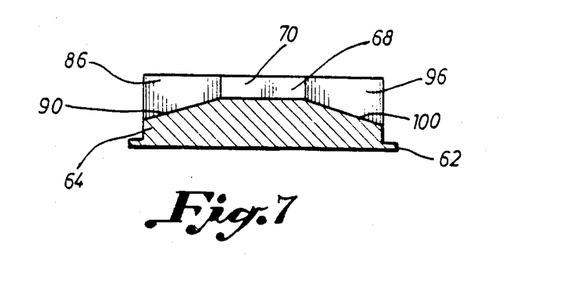
FIG. 7 is a sectional view of the orthodontic bracket illustrated in FIGS. 5 and 6, the section being taken along line 7—7 of FIG. 6.

Referring now to FIGS. 5, 6 and 7, a single/twin orthodontic bracket structure is illustrated generally at 60 which represents an alternative embodiment utilizing the same general principles as are present in the orthodontic bracket structure 10 of FIGS. 1–4. The orthodontic bracket 60, because of its simplicity of design and structure, may be a preferred embodiment from the standpoint of manufacture and commercial use. As shown, the orthodontic bracket 60 incorporates a base structure 62 that is adapted to be secured to the tooth structure of a patient in the same manner as the base portion 12 of FIGS. 1–4. A base projection 64 extends from the base portion 62 and may be attached to or formed integrally with the base structure as desired.

The base projection 64 is formed to define an intermediate section 66 having an active archwire slot 68 formed therein and adapted to receive an edgewise archwire in close fitting relation therein according to the edgewise principles of orthodontic therapy. As is evident from FIGS. 6 and 7, the archwire slot 68 is defined by parallel surfaces 70 and 72 and a flat bottom surface 74. With the archwire in contact with the bottom surface 74, the facial surface of the archwire will be positioned in substantial registry with the facial surface 76 of the intermediate archwire active section. It should be borne in mind that the length of the archwire slot 68 is equivalent to the length of an archwire slot of a conventional single bracket.

The projection 64 includes end portions or sections that may be referred to as tie wing sections 78 and 80. Tie wing section 78 defines a pair of tie wings 82 and 84 which extend from the upper portion of the projection and define undercut slots for receiving ligature wires, elastic bands and other securing devices that maintain the archwire in assembly therewith. The tie wing section 78 is also formed to define a pair of diverging surfaces 86 and 88 that cooperate with an inwardly inclined surface 90 to form an archwire groove or relief that is oriented in contiguous relation with the archwire slot 68. At the opposite end of the bracket structure, the tie wing section 80 is formed to define a pair of tie wings 92 and 94 that are similar to the tie wings 82 and 84. The tie wing section 80 also defines a pair of diverging surfaces 96 and 98 that cooperate with an inwardly inclined bottom surface 100 to define an archwire receiving groove or relief that is also oriented in contiguous relation with the archwire slot 68.

Figure 8:
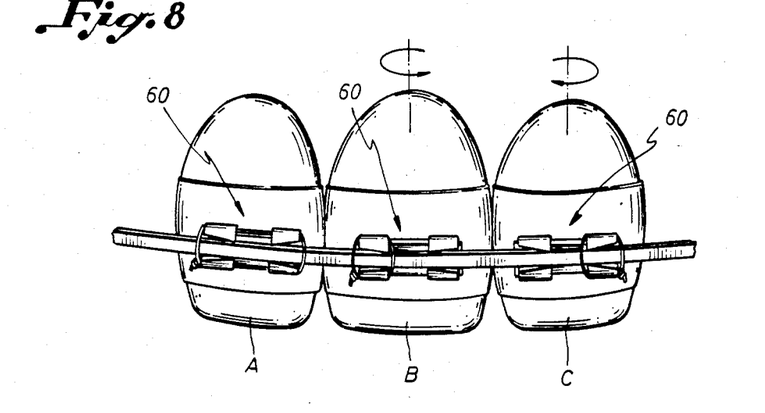
FIG. 8 is a partial view illustrating the teeth of a patient being fitted with an orthodontic appliance having brackets of the form shown in FIGS. 5-7 and embodying the principles of this invention.

The orthodontic bracket structure 60 shown in FIGS. 5-7 functions in an identical manner as compared to the orthodontic bracket 10 shown in FIGS. 1-4. The centrally oriented archwire slot 68 of the intermediate archwire active portion of the bracket structure is of limited length and functions in substantially the same manner as the archwire slot of a single orthodontic bracket from the standpoint of tipping control and maximum interbracket active archwire length. The archwire relief defined by the diverging archwire grooves in the tie wing sections 78 and 80 of the orthodontic bracket structure provide for effective rotational control and lend efficient over-rotational capability to the bracket structure. The bracket design, therefore, provides the beneficial features of both twin and single bracket systems utilized in accordance with the edgewise orthodontic therapy. In FIG. 8, the teeth of a patient are shown with the orthodontic appliances of this invention attached thereto. When a ligature wire encompasses both of the twin tie wings as at A, rotation is not imparted to the teeth. When one ligature wire is employed as at B and C, rotation is imparted as illustrated by the directional arrows.

Figure 9:
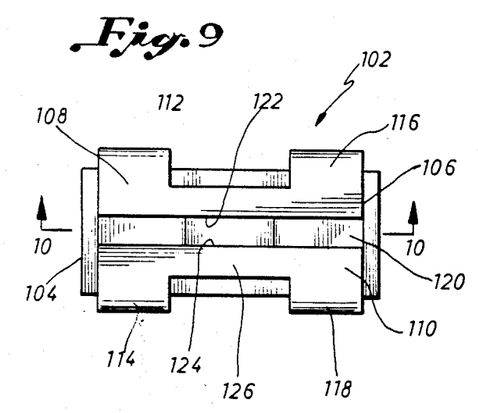
FIG. 9 is a plan view of an orthodontic bracket constructed in accordance with the present invention and representing a further alternative embodiment thereof.
Figure 10:
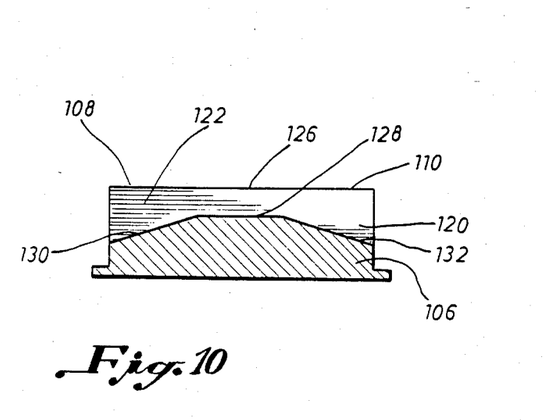
FIG. 10 is a sectional view taken along line 10—10 of FIG. 9.

Under circumstances where the orthodontist desires to utilize conventional twin bracket therapy with which the orthodontist is presently familiar but wishes to also employ a fulcrumming activity for additional rotational control and over-rotational capability, the bracket may conveniently take the form illustrated in FIGS. 9 and 10. The bracket structure illustrated generally at 102 incorporates a base portion 104 from which extends a base projection 106 preferably formed integrally therewith. The projection 106 defines a pair of spaced tie wing sections 108 and 110 that respectively define upper and lower tie wings 112, 114, 116 and 118. The upper portion of the projection 106 is formed to define an elongated archwire slot 120 that extends the entire length of the projection and, therefore, is active with respect to the archwire throughout its entire length. The archwire slot 120 is defined in part by upper and lower parallel surfaces 122 and 124 that have precision engagement with flat surfaces of the rectangular archwire along the entire length of the projection 106. The bracket structure 102 defines a centrally oriented rotational fulcrum portion 126, the length of which is defined by a flat bottom surface 128 of the archwire slot. On either side of the flat bottom surface 128, the archwire slot is formed to incline inwardly or increase in depth providing mesial and distal relief from the surface 128 toward the edges of the bracket by virtue of inwardly tapered surfaces 130 and 132. As the archwire is received within the archwire slot 120, the inner surface of the archwire contacts the fulcrum portion of the bracket, defined by the bottom surface 128. The inwardly tapered surfaces 130 and 132 are relieved from the distal surface portion of the archwire and, therefore, allow bending of the archwire within those portions of the archwire slot that extend beyond the extremities of the bottom surface 128. This feature effectively promotes the rotational control and over-rotation capability of the bracket structure even though the bracket is provided with an active archwire groove extending the entire length of the projection portion of the bracket. This is a feature that is ordinarily beyond the capability of conventional single and twin brackets. The brackets of FIGS. 1–7 also provide for fulcrumming activity in the same manner as the embodiment of FIGS. 9 and 10.

Figure 11:
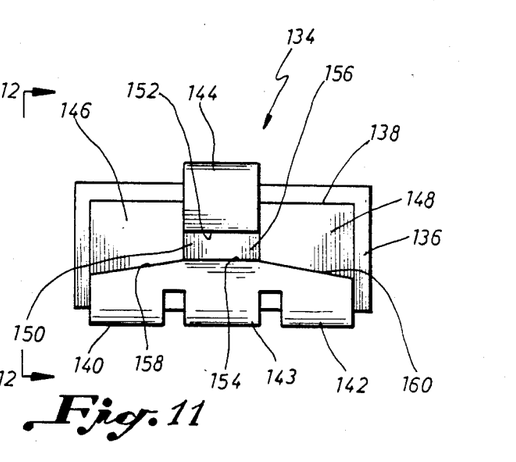
FIG. 11 is a plan view of an orthodontic bracket representing a further alternative embodiment of the present invention wherein an orthodontic bracket incorporating twin ligating tie wing features is also provided with the capability of permitting ample room between bracket structures to permit closing loops and tie-back loops to be utilized between brackets.
Figure 12:
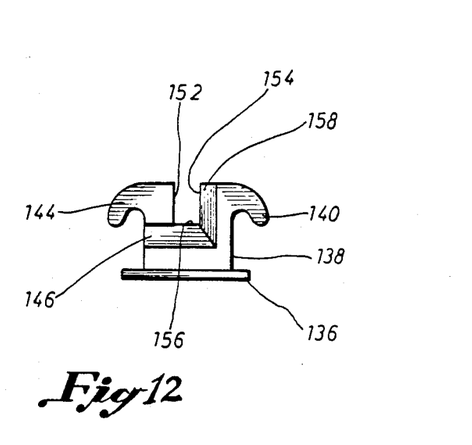
FIG. 12 is an end view of the orthodontic bracket of FIG. 11, the view being taken along line 12—12 of FIG. 11.

Under circumstances where conventional twin brackets are employed in accordance with the edgewise orthodontic technique, the twin tie wings, in addition to the other disadvantages mentioned above, typically minimize the spacing between the tie wings of adjacent brackets such that little or no space is provided for closing loops, tie-back loops and the like. Under circumstances where it is desirable to provide tie-back loops and closing loops, an orthodontic bracket, constructed in accordance with the principles of the present invention, may conveniently take the form illustrated generally at 134 in FIGS. 11 and 12. The bracket structure 134, which may be referred to generally as of "T-bracket" design, incorporates a base structure 136 which is quite similar to the base structures 12 and 62 of orthodontic brackets 10 and 60, described above. A unitary projection 138 extends from the base structure 136 of the bracket and is formed at the upper portion thereof to define spaced ligating tie wings 140 and 142 on either the upper or lower sides of the bracket structure. An intermediate tie wing 143 is positioned between the tie wings 140 and 142 though it use and presence is optional. The tie wings 140 and 142 generally define the respective tie wing end sections of the bracket structure and are ligated for rotational control. On the opposite side of the unitary projection structure 138 is provided a centrally oriented tie wing 144 which extends from an intermediate fulcrum section of the orthodontic bracket. The projection defines relieved portions 146 and 148 on either side of the centrally oriented tie wing 144. The relieved portions of the bracket structure allow the centrally oriented ligating tie wing to define a rather wide space from the adjacent tie wing of the adjacent twin tie wing type orthodontic bracket. This space is ample for the location of tie-back loops and closing loops such as are typically utilized in edgewise orthodontic therapy. At the upper portion of the unitary projection 138 is formed an active archwire slot 150 which is defined by opposed parallel surfaces 152 and 154, together with a flat bottom surface 156. On either side of the archwire slot 150, the projection portion of the bracket structure is formed to define inclined surfaces 158 and 160 that provide relief between the tie wing portions of the bracket structure and the archwire extending through the archwire slot. This archwire relief allows the archwire to have maximum interbracket length to permit a significant amount of bending and twisting capability between the active archwire slots of adjacent orthodontic brackets. Further, the relieved portions 146 and 148 of the bracket structure will be inclined inwardly from the end portions of the archwire slot 150 toward the respective end portions of the unitary projection 138. The central location of the archwire slot 150 and the archwire relief that is provided by the tapering relief surfaces provide the bracket structure 134 with substantially the same degree of extended active interbracket width as is provided by the orthodontic brackets 10 and 60 described above. The single centrally oriented tie wing 144, in addition to providing for closing loops and tie-back loops, may also be utilized in conjunction with the tie wings 140 and 142 to receive ligature wires, elastic elements or the like to secure the archwire within the active archwire slot 150. The intermediate tie wing may be ligated with the single tie wing 144 when rotational control is not necessary. The spacing between the intermediate tie wings and the tie wings 140 and 142 is such that ligature wires may be positioned between the tie wings.

Figure 13:
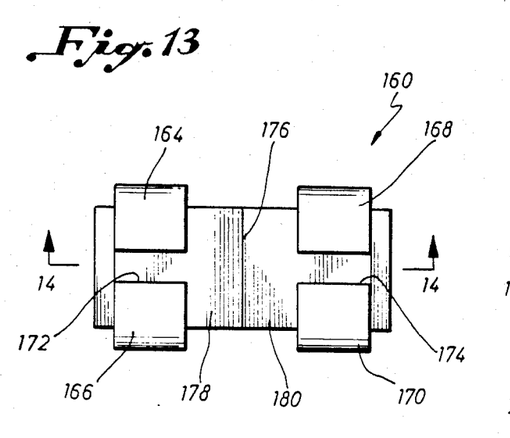
FIG. 13 is a plan view of a simplified orthodontic bracket incorporating the principles of this invention and illustrating a single/twin orthodontic bracket structure with an intermediate archwire active sectiion defined between the twin tie wings.
Figure 14:
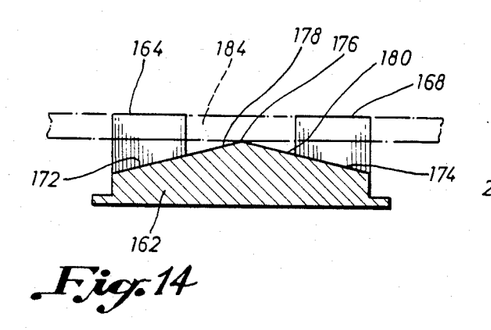
FIG. 14 is a sectional view taken along line 14—14 of FIG. 13.

The present invention may take the form of an alternative embodiment such as shown in FIGS. 13 and 14. An orthodontic bracket, illustrated generally at 160, may incorporate a base structure 162 that is formed to define a pair of twin ligating tie wings 164 and 166 at one extremity thereof and a pair of tie wings 168 and 170 at the opposite end. The tie wing portions of the bracket structure each define a precision archwire slot such as shown at 172 and 174 within which an edgewise archwire is received. Between the tie wing sections of the bracket structure, the base portion 162 defines a fulcrum 176 which may either be a sharply defined ridge, as shown, or, in the alternative, may take the form of any other suitable projecting form. When the archwire is properly seated within the respective archwire grooves 172 and 174 of the tie wing sections, the lingual surface of the archwire is in contact with the fulcrum 176. The upper portion of the archwire may be substantially co-extensive with the upper surface portions of the tie wings. The bracket structure defines inclined surfaces 178 and 180 that extend from the fulcrum 176 toward opposite extremities of the bracket structure. The inclined surfaces 178 and 180 define the bottom portions of the respective archwire slots 172 and 174. As shown in FIG. 14, by way of broken lines, an archwire 182 is positioned in properly seated relation within the archwire slots. The inclined surfaces 178 and 180 diverge from the lingual surface portion of the archwire 182 and thereby provide structural relief in the rotational mode. The archwire may, therefore, be significantly deformed to provide over-rotational capability without archwire interference by the inclined surfaces. Since the fulcrum 176 is in the form of a sharp edge, interbracket width for rotational movement will, therefore, extend from the center-most portion of each of the adjacent orthodontic brackets.

It should be borne in mind that the twin bracket structure illustrated in FIGS. 13 and 14 defines twin tie wings that are of conventional nature thereby enabling the orthodontist to utilize the bracket in conventional manner with which he may already be familiar. The orthodontist will select the mesially and distally relieved bracket structure of FIGS. 13 and 14 under circumstances where the orthodontist also desires to utilize a bracket providing additional rotational capability and over-rotational capability. The archwire is capable of being ligated in the same general manner as with conventional twin brackets and, therefore, the orthodontist need not be required to make any significant modifications in the conventional twin bracket therapy with which he is familiar. When additional rotational control or over-rotational capability is desired, the orthodontist will simply ligate the appropriate mesial or distal tie wing to induce rotation of the bracket and tooth relative to the archwire.

Figure 15:
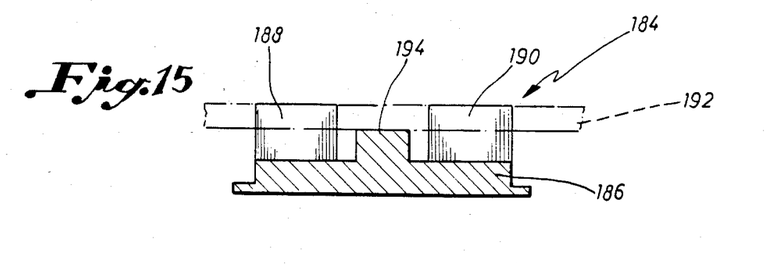
FIG. 15 is a sectional view of an alternative embodiment of the invention representing a variation of the embodiment of FIGS. 13 and 14 wherein the intermediate archwire active section is defined by a generally rectangular projection.

Although the bracket structure of FIGS. 13 and 14 is shown to define a fulcrum in the form of a sharp edge formed by intersecting tapered surfaces 178 and 180, it should be borne in mind that other fulcrum configurations may be employed as well. For example, the embodiment of FIG. 15, which is shown in a sectional view similar to that of FIG. 14, includes an intermediate fulcrum section in the form of a projection of generally rectangular form. As shown in FIG. 15, the bracket is shown generally at 184 and incorporates a base structure 186 that is adapted to be secured in immovable relation with a tooth in the manner disclosed above in the various embodiments of FIGS. 1–14. The upper portion of the base 186 defines pairs of tie wings 188 and 190 of a configuration similar to that of FIG. 13, the tie wings being oriented to define precision archwire slots therebetween. An archwire 192 is shown in broken line in proper position within the precision archwire slots.

Between the pairs of tie wings 188 and 190, the base portion 186 defines an intermediate section 194 of generally rectangular configuration. The intermediate section 194 is pivotal relative to the archwire 192 within limits defined by the mesial-distal relief afforded by the depth of the archwire slots on each side of the rather wide intermediate section. The flat surface 194, being of greater width than the sharp edge 176 of FIG. 13, limits interbracket width by a few thousandths of an inch. For effective rotational capability, a twin bracket must provide a lever arm having sufficient length from the pivot area of the bracket to the adjacent tie wings that mesial or distal ligation develops a proper amount of archwire deformation. The archwire reacts with the pivot area of the bracket to develop a rotational force on the tooth which force dissipates as the tooth is rotated and the archwire returns to its normally arched configuration. Under circumstances where the bracket is of sufficient length, a rather wide pivot area projection may be employed without unduly minimizing the length of the lever arm. For brackets of restricted length, however, a rather narrow or sharp edged pivot area might be required to provide a lever arm of adequate length for effective rotation. It is considered that the rectangular projection 194 may be much easier and less expensive to machine or cast and, therefore, might be preferable from a commercial standpoint.

Figure 16:
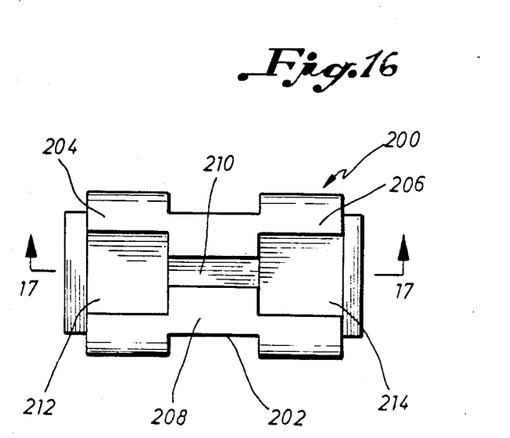
FIG. 16 is an elevational view of another embodiment of this invention representing a variation of the bracket structure of FIGS. 6 and 7 wherein the archwire relief groove is of generally rectangular form.
Figure 17:
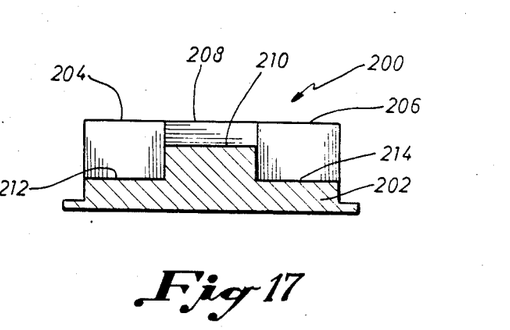
FIG. 17 is a sectional view take along line 17—17 of FIG. 16.

In FIGS. 1–7, each of the bracket configurations includes archwire relief grooves of diverging configuration. As mentioned above, the archwire relief grooves may take any suitable form within the spirit and scope of this invention. As shown in FIGS. 16 and 17, an orthodontic bracket is illustrated generally at 200 which incorporates a base structure 202 forming spaced tie wing sections 204 and 206. Each of the tie wing sections defines a pair of tie wings that are adapted to receive ligating devices or auxiliaries in the manner set forth hereinabove. The intermediate archwire active portion of the base structure 202 defines a precision active archwire slot 210 in generally the same manner as described above in connection with FIGS. 1–7. The bracket base 202 is also formed to define generally rectangular archwire receiving grooves 212 and 214 that are in registry with respective end portions of the archwire slot 210. The archwire grooves 212 and 214 are of sufficient occlusalgingival width and mesial-distal depth in comparison to the archwire slot 210 that a substantial amount of archwire relief is provided at each of the extremities of the archwire slot. The archwire relief defined by these rectangular archwire grooves is the same as the archwire relief that is provided by the diverging, flared archwire grooves of FIGS. 1–7.

When archwires are ligated to orthodontic brackets by means of elastic ligature members, it is necessary that the ligature members apply force moments to the archwire causing it to be retained firmly within the archwire groove of the bracket. In cases where the archwire groove is severly angulated relative to the bracket structure for application of torque forces, the elastic ligature members frequently do not apply sufficient force moments against the archwire wherein such moments are also in registry with the direction of archwire slot angulation. In this case, the archwire will be retained within the archwire groove by insufficient force moments of the elastic ligature member and at times will become inadvertently separated from the archwire slot. When this occurs, of course, the torque force activity ordinarily induced by the rectangular edgewise archwire is lost and will not be resumed unless the archwire is again forced within its angulated slot.

Figures 18, 19, 20, 21:
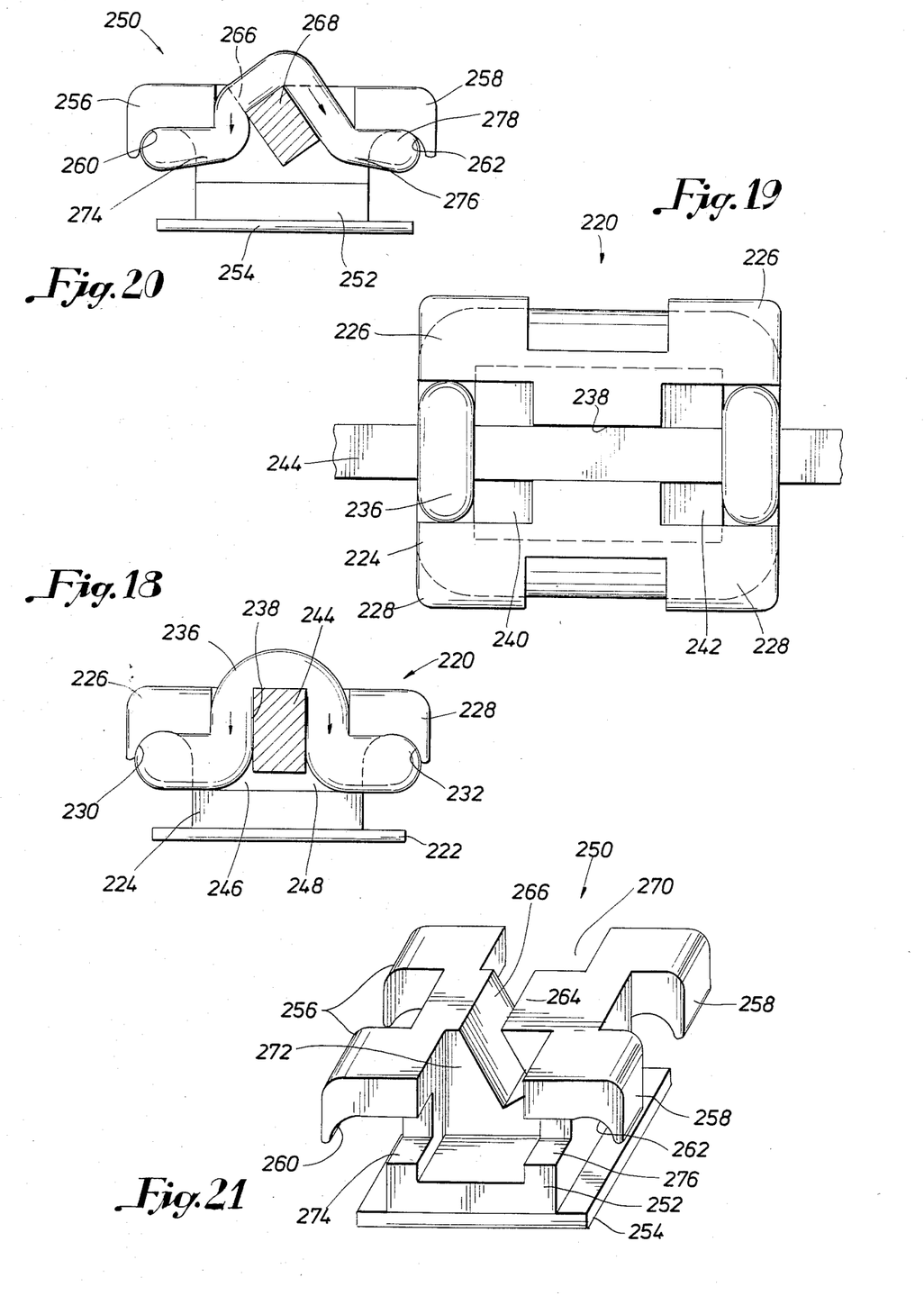
FIG. 18 is an end view of a single/twin orthodontic bracket representing another embodiment of this invention with an elastic ligature member securing an edgewise archwire within the archwire slot of the bracket and wherein the archwire slot and archwire are shown in severely angulated position such as for lingual application.
FIG. 19 is a front elevational view of a single/twin edgewise orthodontic bracket structure similar to that of FIG. 18 and with the archwire slot being less angulated as compared to FIG. 18.
FIG. 20 is an end view of the single/twin edgewise orthodontic bracket of FIG. 18 wherein the bracket incorporates a severely angulated archwire slot such as would be provided in lingual application.
FIG. 21 is an isometric view of the orthodontic bracket of FIG. 18 shown in absence of the archwire and elastic ligature member.

FIGS. 18 and 19 disclose an orthodontic bracket structure of the twin/single type according to the present invention, wherein the bracket structure is efficiently designed to provide directionally oriented force vectors by the elastic ligature member which efficiently maintain the archwire seated firmly in its archwire slot. The bracket structure illustrated generally at 220 is provided with a bonding base, 222, to permit bonding of the bracket directly to the enamel surface of a patient's tooth. Obviously, the bracket may also be secured to a metal band for band type retention to the patient's tooth in the event such is desired. The bracket incorporates a body structure, 224, defining opposed pairs of tie wings, 226 and 228, which define undercut shoulders, 230 and 232 respectively, that provide for retention of an elastic ligature member, 236, in the manner shown in FIGS. 18 and 19.

The body structure of the bracket is also formed to define an intermediate edgewise archwire slot, 238, of rectangular cross sectional form which is of a length approximating that of a typical single type orthodontic bracket. On either side of the archwire slot, 238, is formed archwire relief areas, 240 and 242, which extend from the respective ends of the archwire slot to the proximal edges of the bracket. These archwire relief areas permit flexing of the archwire, 244, from the respective edges of the archwire slot in the manner described above. The total length of the bracket structure 220, approximates that of conventional twin type orthodontic brackets, thereby providing the orthodontist with the combined features of both twin and single type orthodontic brackets.

To provide for efficient seating of the archwire, 244, within the archwire slot, 238, and to promote efficient application of force vectors to the archwire to maintain it firmly seated within the archwire slot, 238, the bracket structure is formed to define ligature slots such as shown at 246 and 248 in FIG. 18 and 274 and 276 in FIGS. 20 and 21. As shown in FIG. 18, the slots 246 and 248 intersect the relief area, 240, at one end of the bracket struture. With an elastic ligature member secured about the opposed tie wings, and being received within the ligature slots, it will be forced to the configuration shown in FIGS. 18 and 19. The elastic ligature element will therefore apply force vectors essentially as shown by the force arrows in FIG. 18, thereby causing the rectangular archwire, 244, to be urged in a direction with is aligned with the archwire slot, 238.

The problem of archwire seating becomes more severe under circumstances where the archwire slot is severely angulated with respect to other components of the bracket structure such as in the case of certain tooth installation for lingual orthodontic appliance. For example, as shown in FIGS. 20 and 21, a single/twin type orthodontic bracket is provided according to the edgewise technique wherein the edgewise archwire slot is severely angulated, i.e., in the order of 45°, to thereby permit placement on the lingual surface of some teeth. The bracket structure of FIGS. 20 and 21 is illustrated generally at 250 and incorporates a body structure, 252, to which a bonding base, 254, may be secured. The body structure defines opposed spaced pairs of tie wings, 256 and 258, which are each undercut to form ligature retention shoulders, 260 and 262.

Between the pairs of tie wings the body structure also defines an intermediate body section, 264, which forms an angulated archwire slot, 266, for retention of an edgewise archwire, 268, of rectangular cross sectional configuration in the angulated manner shown in FIG. 20. On either side of the archwire slot, 266, the body structure defines archwire relief areas, 270 and 272, which effectively provide for structural clearance about the archwire beyond the extremities of the archwire slot, 266. The archwire slot is of approximately the same length as the archwire slot of a conventional single edgewise orthodontic bracket, thereby providing for approximately the same interbracket width between the archwire slots of adjacent brackets as is the case with single tie wing brackets. The bracket structure of FIG. 21 is shown in absence of an elastic ligature member to more readily facilitate understanding of the bracket structure. The archwire slot, 266, is shown to have parallel side surfaces for force transmitting structural relationship with the rectangular archwire, 268, according to the edgewise technique.

Especially in the case of severly angulated archwire slots, such as shown in FIGS. 20 and 21, it is desirable that ligature members, especially elastic type ligature members, establish proper force vectors between the bracket and archwire to maintain the archwire firmly seated within the archwire slot. In the cases of typical orthodontic brackets incorporating twin tie wings, the force vectors applied by ligature members to the archwire are not so oriented as to establish firm seating of the archwire within the archwire slot. Accordingly, the bracket structure of FIGS. 20 and 21 is formed to define transverse ligature grooves such as shown at 274 and 276. An elastic ligature member such as shown at 278 in FIG. 20, extends beneath the undercut tie wing shoulders, 260 and 262, and then passes through the transverse ligature slots, 274 and 276, at each extremity of the bracket. The ligature member then extends through the relief area of the bracket structure and over the archwire, 268, located in the archwire slot. Even with the archwire severely angulated, as shown in FIGS. 20 and 21, the elastic ligature member will develop force vectors as shown by the force arrows in FIG. 20 which are approximately aligned with the inclined side surfaces of the archwire. These force vectors cooperate to maintain the angulated archwire, 268, firmly seated within the archwire slot, 266. The bracket structures of FIGS. 18 through 21, therefore, provides for efficient archwire retention and minimize the possibility that the archwire might become unseated from the archwire slot.

In view of the foregoing, it is apparent that I have provided a combination single/twin orthodontic bracket system which effectively incorporates the advantageous capabilities of both single and twin type orthodontic brackets. This orthodontic bracket system provides effective interbracket spacing of maximum length which is ordinarily unavailable in twin orthodontic brackets. The edgewise orthodontic technique is efficiently employed in such manner as to provide efficient tipping control and to further provide efficient rotational and over-rotational capability; combined features which are ordinarily unavailable in either single or twin orthodontic bracket systems. The present invention provides an orthodontic bracket structure according to the edgewise technique which may be utilized to provide an effective rotation and over-rotational capability as well as the usual tipping and torquing capability that is effective in single tie wing type bracket systems. The centrally oriented archwire active portion of the bracket structure defines a precision active archwire slot that renders the bracket system effective in accordance with the edgewise orthodontic therapy technique. Additionally, archwire relief grooves at outer portions of the bracket structure are flared in width to increase the flexibility of the archwire by increasing interbracket width and are flared in depth to promote the rotational and over-rotational control capability of the bracket. The single/twin edgewise bracket structure set forth herein also provides for the development of efficient force vectors between the ligature members and archwire to ensure firm archwire seating even though the archwire slots may be severely angulated. In view of the foregoing, it is thus apparent that the present invention is one well adapted to attain all of the objects and features hereinabove set forth, together with other features which are inherent in the description of the apparatus itself.

While the foregoing is directed to the preferred embodiments of the present invention, other and further embodiments of the invention may be devised without departing from the basic concept thereof, and the scope thereof is determined by the claims which follow.

What is claimed is:

1. A combination single/twin orthodontic bracket for edgewise orthodontic therapy, said orthodontic bracket comprising:
    (a) bracket body means adapted to be secured in immovable relation with a tooth and forming mesial and distal sides and occlusal and gingival portions;
    (b) occlusal tie wing means extending from said occlusal portion of said bracket body means;
    (c) gingival tie wing means extending from said gingival portion of said bracket body means, said occlusal and gingival tie wing means defining a specified tie wing length;
    (d) an intermediate bracket section being positioned at least partially between said occlusal and gingival tie wing means, said intermediate bracket section defining spaced parallel planar archwire engaging surfaces according to edgewise orthodontic therapy which form a precision edgewise archwire slot of less length than said specified tie wing length and adapted to receive an edgewise archwire of rectangular configuration in precision interfitting force transmitting relation such that forces are imparted by said archwire to said bracket body means according to edgewise orthodontic therapy; and
    (e) said bracket body means defining archwire relief surface means being greater in occlusal gingival width as compared to said archwire slot and extending from each end of said archwire slot of said intermediate section to the respective mesial and distal sides of said bracket body means and being located at least partially between said occlusal and gingival tie wing means, whereby force transmission from the archwire to said bracket body means for tipping and torquing takes place at said edgewise archwire slot of said intermediate bracket section, interbracket width of the archwire extends between the intermediate bracket sections of adjacent brackets and said tie wing means are selectively ligated for rotational control.

2. A combination single/twin orthodontic bracket as recited in claim 1, wherein:
    said archwire relief groove means is of greater buccal-lingual depth as compared to said archwire slot.

3. A combination single/twin orthodontic bracket as recited in claim 1, wherein said tie wing means comprises:
    (a) a pair of spaced tie wings being defined on at least one of the occlusal and gingival portions of said bracket body means; and
    (b) said archwire slot of said intermediate bracket section being located at least in part between said spaced tie wings.

4. A combination single/twin orthodontic bracket as recited in claim 1, wherein said tie wing means comprises:
    (a) a pair of spaced tie wings being positioned in spaced relation on at least one of the occlusal and gingival portions of said bracket body means;
    (b) at least one tie wing being located on the other of said occlusal and gingival portions of said bracket body means; and
    (c) said intermediate bracket section being located at least in part between said pair of spaced tie wings and also being located at least in part between said pair of spaced tie wings and said at least one tie wing.

5. A combination single/twin orthodontic bracket as recited in claim 1, wherein said occlusal and gingival tie wing means comprises;
    (a) occlusal and gingival pairs of tie wings extending from said bracket body means, each of said occlusal and gingival pairs of tie wings beng disposed in spaced relation on respective occlusal and gingival portions of said bracket body means;

(b) said archwire relief surface means defining archwire relief grooves between occlusal and gingival ones of each of said pairs of occlusal and gingival tie wings, said archwire relief grooves being contiguous with said archwire slot and receiving said edgewise archwire in inactive relieved manner therein; and (c) said intermediate bracket section being located at least in part between each of said occlusal and gingival pairs of tie wings, whereby the intermediate bracket sections of adjacent similar orthodontic brackets define the limits of active interbracket archwire length between brackets at least in the torquing and tipping planes.

6. A combination single/twin orthodontic bracket as recited in claim 5, wherein:

said archwire relief grooves each define archwire relief in both occlusal-gingival width and buccal-lingual depth and are in registry with said archwire slot.

7. A combination single/twin orthodontic bracket as recited in claim 1, wherein:

(a) said archwire slot extends at least a portion of said specified tie wing length and includes archwire slot portions relieved in mesial and distal depth at each extremity thereof; and (b) a fulcrum structure is defined within said archwire slot between said relieved portions of said archwire slot.

8. A combination single/twin orthodontic bracket for edgewise orthodontic therapy, said orthodontic bracket comprising:

(a) bracket body means adapted to be secured in immovable relation with a tooth and forming mesial and distal sides and occlusal and gingival portions;

(b) a pair of spaced rigid tie wing means extending from at least one of said occlusal and gingival portions of said bracket body means and defining a specified tie wing length;

(c) at least one rigid tie wing extending from the opposite one of said occlusal and gingival portions of said bracket body means;

(d) an intermediate bracket section being formed by said bracket body and positioned at least partially between said pair of spaced tie wing means and being of less length as compared to said specified tie wing length, said intermediate bracket section defining spaced parallel planar archwire engaging surfaces according to edgewise orthodontic therapy, said parallel planar archwire engaging surfaces defining a precision active archwire slot of less length as compared to said specified tie wing length, said archwire slot adapted to receive an edgewise archwire of rectangular cross-sectional configuration in active force transmitting relation therein with opposed planar surfaces of said edgewise archwire in engaging force transmitting relation with said parallel planar archwire engaging surfaces according to edgewise orthodontic therapy such that tooth moving forces are imparted by said archwire to said intermediate bracket section of said bracket body means in the tipping and torquing plane, and (e) said bracket body means forming relief surface means defining occlusal-gingival archwire relief at each end of said archwire slot of said intermediate bracket section and extending respectively to said mesial and distal sides, said archwire relief surface means being spaced from said archwire, whereby interbracket archwire length in at least the torquing and tipping planes extends from said archwire slot of said intermediate bracket section to the archwire slot of an adjacent similar bracket and force transmission from said archwire to said bracket body occurs at said archwire slot of said intermediate bracket section in the tipping and torquing planes.

9. An orthodontic bracket as recited in claim 8, wherein:

said at least one tie wing extends from the intermediate portion of said bracket body means and cooperates with said bracket body means to define said intermediate bracket section and said archwire slot.

10. An orthodontic bracket as recited in claim 8, wherein:

said relief surface means being located between said bracket body means and define outwardly diverging flared archwire relief groove means being in registry with said archwire slot of said intermediate bracket section, said archwire relief groove means defining said archwire relief and extending to respective mesial and distal sides of said bracket body means.

11. An orthodontic bracket as recited in claim 10, wherein:

said outwardly diverging flared archwire relief groove means is flared in both occlusal-gingival width and buccal-lingual depth.

12. An orthodontic bracket as recited in claim 8, wherein:

said tie wing means on at least one of said occlusal and gingival portions of said bracket body means and cooperatively forms at least a portion of said archwire relief means.

13. An orthodontic bracket as recited in claim 8, wherein:

(a) said at least one tie wing is a single tie wing located centrally of said bracket body means and extending from said intermediate bracket section; and (b) an intermediate tie wing is positioned between said pair of spaced tie wings and is in opposed ligating registry with said at least one tie wing.

14. A combination twin/single orthodontic bracket for use in edgewise orthodontic therapy, said bracket comprising:

(a) bracket body means adapted to be secured in immovable relation with a tooth and forming a specified bracket length; and (b) at least one projection means extending from an intermediate portion of said bracket body means, said projection means defining:

(1) an intermediate bracket section of single bracket length located intermediate the extremities of said projection means, said intermediate bracket section defining spaced parallel planar archwire engaging surfaces according to edgewise orthodontic therapy, said parallel planar archwire engaging surfaces forming a precision active archwire slot of less length than said specified bracket length and having first and second extremities, said archwire slot adapted to receive an edgewise archwire of rectangular cross-sectional configuration such that opposed parallel planar surfaces of the archwire are in force transmitting relation with said parallel planar surfaces of said intermediate bracket section;

(2) said at least one projection means defining archwire relief surface means cooperatively forming archwire relief means extending from said first and second extremities of said archwire slot and terminating at respective ends of said bracket body means, said archwire relief means being in registry with said archwire slot whereby force transmission from the archwire to said bracket body for tipping and torquing takes place at said archwire slot of said intermediate bracket section and interbracket width of the archwire extends between the intermediate bracket sections of adjacent brackets;

(3) a pair of spaced occlusal tie wings being located on one side of said archwire slot and archwire relief means; and (4) a pair of spaced gingival tie wings being located on the opposite side of said archwire slot and archwire relief means, said intermediate bracket section being positioned in centralized relation with said occlusal and gingival tie wings, whereby said tie wings are selectively ligated to induce rotational forces to said at least one projecting means.

15. A combination single/twin orthodontic bracket as recited in claim 14, wherein:
(a) said precision active archwire slot and said archwire relief means cooperatively receive said edgewise archwire; and
(b) said archwire relief surface means are positioned between occlusal and gingival pairs of tie wings and cooperate to define said archwire relief means therebetween.

16. An orthodontic bracket as recited in claim 14, wherein:
said projection means forms a pair of archwire relief grooves located on opposite ends of said archwire slot each groove being contiguous with said archwire slot and each defining archwire relief in both occlusal-gingival width and buccal-lingual depth from said archwire slot toward the mesial and distal edges of said projection means.

17. A combination single/twin orthodontic bracket for edgewise orthodontic therapy, said orthodontic bracket comprising:
(a) bracket body means adapted to be secured in immovable relation with a tooth and forming mesial and distal sides;
(b) an intermediate projection being defined by said bracket body means and located intermediate said mesial and distal sides of said bracket body means, said intermediate projection adapted to receive an edgewise archwire in contacting relation therewith;
(c) occlusal and gingival pairs of tie wings being defined by said bracket body means and being positioned on opposed sides of said intermediate projection; and
(d) said bracket body between said occlusal and gingival tie wings cooperatively defining precision active archwire slot means on opposed mesial and distal sides of said intermediate projection, each of said archwire slot means being defined by spaced parallel planar surfaces formed by said bracket body means between respective occlusal and distal tie wings and adapted to receive an edgewise archwire of rectangular cross-sectional configuration such that parallel planar surfaces of said edgewise archwire are in engaging, force transmitting relation with said parallel planar surfaces of said archwire slot means according to edgewise orthodontic therapy, said archwire slot means being of greater buccal-lingual depth as compared to said intermediate projection and defining buccal-lingual archwire relief permitting bracket and tooth rotation about said intermediate projection, whereby force transmission from said archwire to said bracket occurs at said archwire slot means and said archwire relief permits rotation of said bracket about said intermediate projection through selective ligation of said tie wings.

18. A combination single/twin orthodontic bracket as recited in claim 17, wherein:
said bracket body means defines a pair of inclined substantially planar surfaces intersecting at the central portion of said intermediate projection of said bracket body means and defining fulcrum means, for engagement by said archwire.

19. A combination twin/single orthodontic bracket for edgewise orthodontic therapy, said orthodontic bracket comprising:
(a) bracket body means adapted to be secured in immovable relation with a tooth and forming occlusal and gingival bracket portions;
(b) a pair of spaced tie wing means extending from at least one of the occlusal and gingival bracket portions of said bracket body means and defining a specified twin bracket tie wing length;
(c) a single tie wing extending from the central portion of the opposite one of said occlusal and gingival bracket portions of said bracket body means;
(d) an intermediate projection being formed between said pair of spaced tie wing means and being of less length as compared to said specified twin bracket tie wing length, said single tie wing and said intermediate projection cooperating to define a precision active archwire slot of less length as compared to said specified twin bracket tie wing length, said archwire slot being formed by spaced parallel planar surfaces of said intermediate projection adapted to receive an edgewise archwire therein of rectangular cross-sectional configuration such that parallel planar surfaces of said archwire are disposed in force transmitting engagement with said parallel planar surfaces of said intermediate projection; and
(e) said bracket body means defining occluso-gingival archwire relief extending from respective ends of said active archwire slot to the respective sides of said bracket body means.

20. An orthodontic bracket for edgewise orthodontic therapy, said orthodontic bracket comprising:
(a) bracket body means adapted to be secured in immovable relation with a tooth;
(b) twin pairs of spaced rigid tie wings extending from said bracket body means and defining a pair of mesially-distally spaced precision active archwire slots, each of said spaced precision active archwire slots being defined by spaced parallel planar surfaces of said tie wing means and adapted to receive an edgewise archwire therebetween of rectangular cross-sectional configuration such that parallel planar surfaces of said edgewise archwire are disposed in force transmitting engagement with said parallel planar surfaces of said tie wing means according to edgewise orthodontic therapy; and (c) fulcrum surface means being formed intermediate said pairs of spaced tie wing means and intermediate said precision active archwire slots, said fulcrum surface means being engaged by said archwire such that bracket and tooth rotation occurs about said fulcrum means, said archwire slots each defining buccal-lingual archwire relief relative to said fulcrum surface means, whereby force transmission between said archwire and said bracket takes place at said spaced precision active archwire slots and said buccal-lingual archwire relief permits rotation of said bracket through selective ligation of said tie wing means.

21. An orthodontic bracket for edgewise orthodontic therapy, comprising:
(a) bracket body means for attachment to the tooth of a patient and defining an intermediate bracket section forming elongated archwire slot means of rectangular cross-sectional configuration, said body means further defining distal and mesial extremities extending beyond said intermediate bracket section;
(b) tie wing means extending gingivally and occlusally from said bracket body means and forming undercut ligature retaining shoulders; and
(c) said bracket body means defining archwire relief surface means extending mesially and distally beyond said intermediate bracket section and forming occlusal gingival archwire relief, whereby force transmission from said archwire to said bracket occurs at said edgewire archwire slot means and said archwire relief permits selective rotation of said bracket through selective ligation of said tie wing means, said bracket body means defining ligature groove means at said proximal and distal extremities thereof, said ligature groove means extending transversely of said archwire slot means and being positioned at least partially beneath said tie wing means and receiving a ligature member passing over an edgewise archwire in said archwire slot means and extending beneath said tie wing means such that force vectors applied by said ligature members to said archwire are closely aligned with the respective parallel side surfaces of the edgewise archwire.

22. An orthodontic bracket as recited in claim 21, wherein:
(a) said bracket body means is in the form of a twin bracket with said tie wing means comprising gingival and occlusal pairs of spaced tie wings defined by said bracket body means;
(b) said bracket body means defines an intermediate bracket section disposed at least partially between said pairs of spaced tie wings, said intermediate bracket section being of less length than the length of said bracket body means and defining an edgewise archwire slot of rectangular cross-sectional configuration extending the length of said intermediate bracket section and being of similar length as the length of the archwire slot in single edgewise brackets; and
(c) said bracket body means defining archwire relief surface means being greater in occlusal-gingival width and buccal-lingual depth as compared to said archwire slot; whereby force transmission from the archwire to said bracket body means for tipping and torquing takes place at said edgewise archwire slot of said intermediate bracket section, interbracket width of the archwire extends between the intermediate bracket sections of adjacent brackets and said tie wing means are selectively ligated for rotational control.

23. An orthodontic bracket as recited in claim 22, wherein:
(a) said body means further defines archwire relief areas on opposite sides of said bracket intermediate bracket section and in registry with the ends of the archwire slot; and
(b) said transverse ligature groove means is defined by groove sections in registry with said archwire relief areas, whereby the ligature member at each side of the body means extends through said ligature groove sections, through said archwire relief areas and over the archwire.

24. An orthodontic bracket as recited in claim 23, wherein:
said archwire relief area is relieved occlusally, gingivally, mesially and distally, wherein active interbracket width of the archwire of adjacent similar brackets extends from the ends of the edgewise archwire slots formed therein.

25. A combination single/twin orthodontic bracket for edgewise orthodontic therapy, comprising:
(a) a bracket body adapted to be secured in immovable relation with a tooth and forming occlusal and gingival portions and mesial and distal sides;
(b) pairs of rigid gingival and occlusal tie wings being formed by said bracket body;
(c) an intermediate bracket section being formed by said bracket body and being located between said gingival and occlusal pairs of tie wings, said intermediate bracket section forming spaced parallel planar surfaces and a bottom surface defining an edgewise archwire slot of rectangular cross-sectional configuration; and
(d) said bracket body forming a relief groove bottom surface and relief groove side surfaces extending from respective ends of said edgewise archwire slot to respective mesial and distal sides of said bracket body and cooperatively forming a pair of archwire relief grooves contiguous with respective ends of said edgewise archwire slot and being of greater occlusal-gingival width than said archwire slot from the ends of said archwire slot to said mesial and distal sides of said bracket body, whereby force transmission from the archwire to said bracket body for tipping and torquing takes place at said archwire slot of said intermediate bracket section, interbracket width of the archwire extends between the intermediate bracket sections of adjacent brackets and said tie wing means are selectively ligated for efficient rotational control.

26. A combination single/twin orthodontic bracket for edgewise orthodontic therapy as recited in claim 25, wherein:
said archwire relief grooves define archwire relief both occlusally and gingivally.

27. A combination single/twin orthodontic bracket for edgewise orthodontic therapy as recited in claim 25, wherein:
said archwire relief grooves define archwire relief bucco-lingually and occluso-gingivally.

28. A combination single/twin orthodontic bracket for edgewise orthodontic therapy as recited in claim 25, wherein:

said relief groove bottom surface is coplanar with said bottom surface of said archwire slot.

29. A combination single/twin orthodontic bracket for edgewise orthodontic therapy as recited in claim 25, wherein:

said relief groove bottom surfaces extend lingually of said bottom surface of said archwise slot and provide inaccurate buccal-lingual archwire relief from the ends of said archwire slot to said mesial and distal sides of said bracket body.

* * * * *